US011545270B1

(12) United States Patent
Frey et al.

(10) Patent No.: US 11,545,270 B1
(45) Date of Patent: Jan. 3, 2023

(54) DOSSIER CHANGE CONTROL MANAGEMENT SYSTEM

(71) Applicant: Merck Sharp & Dohme Corp., Rahway, NJ (US)

(72) Inventors: Christina Elizabeth Frey, Limerick, PA (US); Andrew Hakfan Chen, Lansdale, PA (US); Christopher Michael Lee, Lansdale, PA (US); Nirdosh Jagota, Malvern, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 48 days.

(21) Appl. No.: 16/748,800

(22) Filed: Jan. 21, 2020

Related U.S. Application Data

(60) Provisional application No. 62/794,923, filed on Jan. 21, 2019.

(51) Int. Cl.
G16H 70/40 (2018.01)
G16H 20/10 (2018.01)

(52) U.S. Cl.
CPC ............ *G16H 70/40* (2018.01); *G16H 20/10* (2018.01)

(58) Field of Classification Search
CPC .................................................... G16H 70/40
See application file for complete search history.

(56) References Cited

U.S. PATENT DOCUMENTS

| 6,854,086 | B2* | 2/2005 | Umen | G06Q 30/02 715/236 |
| 8,645,180 | B1* | 2/2014 | Zeng | G06Q 10/06 705/7.19 |
| 2003/0036942 | A1* | 2/2003 | Wescott | G06Q 10/06313 705/7.23 |
| 2004/0249836 | A1* | 12/2004 | Reynders | G16H 70/40 |
| 2006/0212487 | A1* | 9/2006 | Kennis | G06Q 10/10 |
| 2007/0011183 | A1* | 1/2007 | Langseth | G06F 16/313 707/E17.084 |
| 2007/0185751 | A1* | 8/2007 | Dempers | G16H 70/40 705/7.29 |
| 2007/0271299 | A1* | 11/2007 | Wang | G06Q 50/02 |
| 2011/0179036 | A1* | 7/2011 | French | G06F 40/151 707/739 |
| 2011/0208662 | A1* | 8/2011 | Haunschild | G06Q 30/018 705/317 |
| 2013/0018802 | A1* | 1/2013 | McCormick | G06Q 10/0631 705/301 |

(Continued)

*Primary Examiner* — Evangeline Barr
*Assistant Examiner* — Karen A Hranek
(74) *Attorney, Agent, or Firm* — Fenwick & West LLP

(57) ABSTRACT

A dossier change control management system periodically ingests data regarding a regulated product from multiple data stores. The dossier change control management system updates dossier data describing a dossier history for the regulated product using the received data. The dossier includes multiple documents in a standardized format and is updated based on a data mapping indicating correspondence between fields of the documents and portions of the received data. An out-of-expectation scenario for the dossier is identified based on regulatory requirements and an alert generated. A report with information about the out-of-expectation scenario is provided for display at a client device based on the alert.

19 Claims, 7 Drawing Sheets

(56) References Cited

U.S. PATENT DOCUMENTS

| | | | |
|---|---|---|---|
| 2013/0198094 A1* | 8/2013 | Arazy | G06Q 50/18 |
| | | | 705/317 |
| 2016/0117293 A1* | 4/2016 | Dettman | G06F 40/143 |
| | | | 715/234 |
| 2016/0203494 A1* | 7/2016 | Galligan Davila | G06Q 30/018 |
| | | | 705/317 |
| 2016/0246823 A1* | 8/2016 | Varghes | G06F 16/219 |
| 2017/0083346 A1* | 3/2017 | Frankland | G06Q 10/063 |
| 2017/0103486 A1* | 4/2017 | Cai | G06F 40/30 |
| 2018/0075554 A1* | 3/2018 | Clark | G06Q 50/18 |
| 2018/0307685 A1* | 10/2018 | Sa | G06F 16/2425 |
| 2020/0143277 A1* | 5/2020 | Levine | G06N 7/005 |
| 2020/0175110 A1* | 6/2020 | Snyder | G06F 40/279 |

\* cited by examiner

DOSSIER CHANGE CONTROL MANAGEMENT SYSTEM

CROSS-REFERENCE TO RELATED APPLICATION

This application claims the benefit of U.S. Provisional Patent Application No. 62/794,923, filed Jan. 21, 2019, which is incorporated by reference.

TECHNICAL FIELD

This disclosure relates generally to the field of data management systems and, in particular, to managing quality and regulatory documents for pharmaceutical products across multiple jurisdictions.

BACKGROUND

Many pharmaceutical products are manufactured, sold, and used in multiple jurisdictions. The regulatory requirements vary across jurisdictions and are frequently changing. This makes managing and ensuring conformance with regulatory requirements a challenging task. Existing solutions often involve human operators manually retrieving and checking multiple documents, which may be stored in multiple systems in multiple formats, on a case by case basis. This is time consuming and may result in errors.

BRIEF DESCRIPTION OF DRAWINGS

The disclosed embodiments have advantages and features which will be more readily apparent from the detailed description, the appended claims, and the accompanying figures (or drawings). A brief introduction of the figures is below.

DETAILED DESCRIPTION

Figure 1:
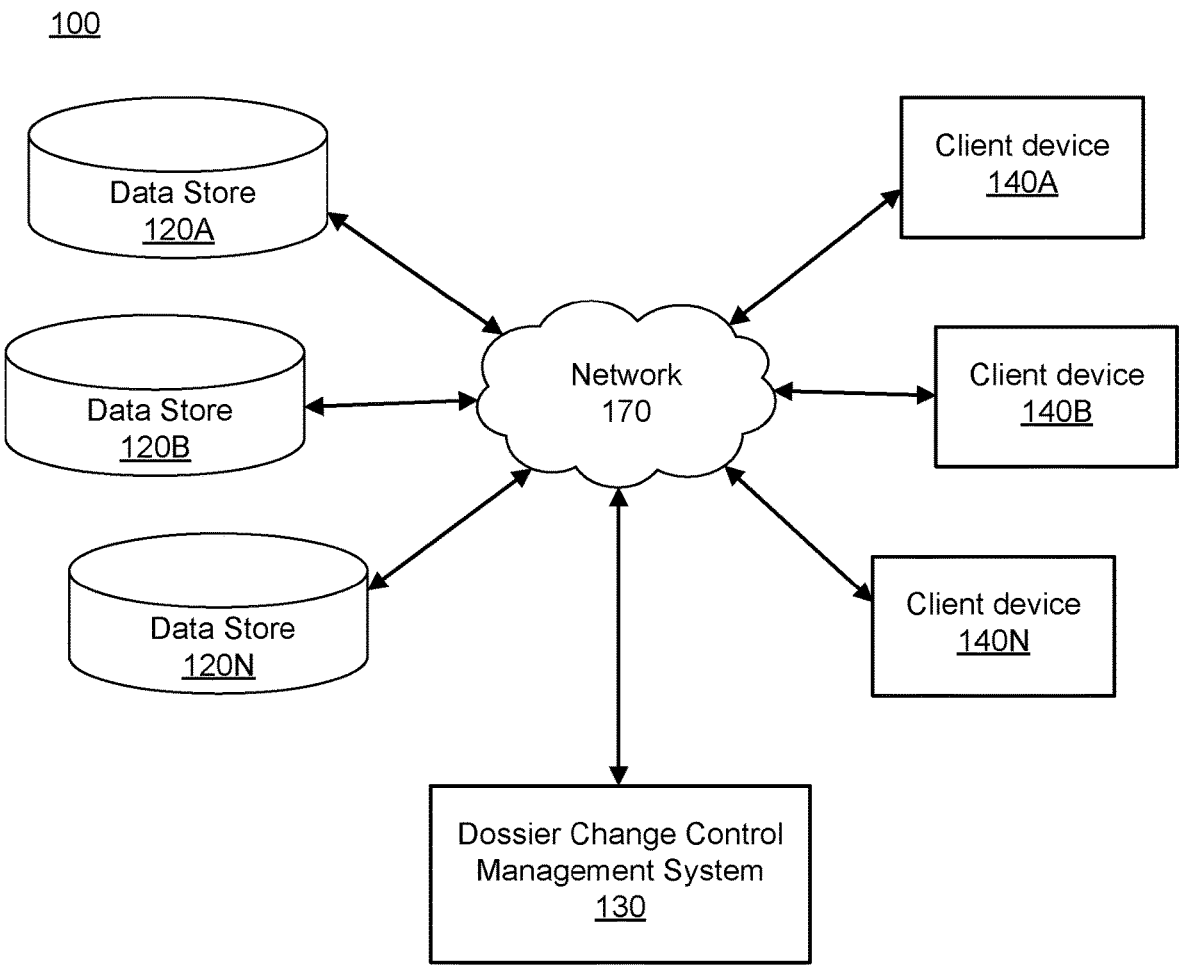
FIG. 1 is a block diagram of a networked computing environment suitable for providing dossier change control management, according to one embodiment.

Reference will now be made in detail to several embodiments, examples of which are illustrated in the accompanying figures. It is noted that wherever practicable similar or like reference numbers may be used in the figures and may indicate similar or like functionality. Where similar or like elements are identified by a common numeral followed by a different letter, a reference to the numeral alone may refer to any such element or combination of such elements (including all such elements). The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

In various embodiments, a dossier change control management system automatically ingests documents from multiple sources and tracks changes in the dossiers for pharmaceutical products in multiple jurisdictions. Each dossier includes aggregated license information for a particular pharmaceutical product in relevant jurisdictions. Thus, among other things, a dossier indicates the status of regulatory submissions for the pharmaceutical product in each relevant jurisdiction. In some cases, the dossiers may be supplemented by manual addition and/or tagging of documents.

The dossier change control management system may identify gaps in a dossier, such as missing metadata that may indicate missing or incomplete documents, and generate an alert to notify the appropriate entity that corrective action should be taken. Among other advantages, this may enable information found in documents from multiple sources in multiple formats to be aggregated and presented to users in a consistent manner. Unlike previous systems, enables gaps to be easily identified, because the available information for a given pharmaceutical product is aggregated in a standardized format, regardless of the original format or source or format of that information.

The dossier change control management system may also generate reports (e.g., for display in a user interface). For example, in one embodiment, a data mapping indicates one or more sources for data to be included in a report. The report may be provided in response to a user query and provide efficient updates regarding the status of regulatory submissions, history of changes to documents, pending action items, potential problems, etc. Among other advantages, this may provide more nuanced and/or understandable views of the available data, improve the efficiency of operators tasked with ensuring regulatory compliance, and reduce computational time and resources spent on servicing individual requests for information from operators attempting to build an overall picture of a product dossier manually.

The dossier change control management system may also provide metrics reports that indicate the overall status of a dossier and provide access to underlying documents. This may help operators quickly identify and address problems within a dossier.

System Overview

FIG. 1 illustrates one embodiment of a networked computing environment 100 suitable for providing dossier change control management. In the embodiment shown, the networked computing environment 100 includes a set of data stores 120, a dossier change control management system 130, and a set of client devices 140, all connected via a network 170. Although three data stores 120 and client devices 140 are shown, in practice, the networked computing environment may include any number of data stores and client devices. In other embodiments, the networked computing environment 100 contains different and/or additional elements. In addition, the functions may be distributed among the elements in a different manner than described.

The data stores 120 include one or more machine-readable media (e.g., non-transitory computer-readable media) configured to store quality control and regulatory documents for pharmaceutical products. For example, one data store 120A might be a database of documents submitted to regulators by an entity and another data store 120B might be a database of documents received from health authorities (e.g., questions, approvals, etc.). Other data stores 120 can include quality control data, clinical trial results, and the like. In some embodiments, different submissions to and/or documents received from different regulators (e.g., for different jurisdictions) may be stored in different data stores. The data stores 120 may store structured data, unstructured data, or a mixture of both. The data stores 120 may store data in different formats and store different data for similar purposes (e.g., different regulatory authorities may each use their own data format and require different content for regulatory submissions).

The dossier change control management system 130 ingests data from the data stores 120 to monitor dossiers for pharmaceutical products in one or more jurisdictions along with corresponding change histories. The dossier change control management system 130 also provides tools (e.g., via an API) for client devices 140 to view reports generated from product dossiers. The dossier change control management system 130 may also provide notifications or alerts (e.g., to a subscribed client device 140) on detection of out-of-expectation scenarios for a dossier (e.g., if an expected regulatory filing is not added to a dossier or expected data is missing or incomplete in a filing). This may enable corrective action to be quickly taken to address the out-of-expectation scenario. Various embodiments of the dossier change control management system 130 are described in greater detail below, with reference to FIG. 2.

The client devices 140 are computing devices with which users may access data and functionality provided by the dossier change control management system 130. The client devices 140 are computing devices capable of receiving user input as well as transmitting and receiving data via the network 170. In one embodiment, a client device 140 is a computer system, such as a desktop or a laptop computer. Alternatively, a client device 140 may be a device having computer functionality, such as a personal digital assistant (PDA), a mobile telephone, a smartphone, or other suitable device. A client device 140 may execute software (e.g., an application) enabling a user of the client device 140 to interact with the dossier change control management system 130 to add documents, provide information to address identified gaps, and/or access reports. For example, a client device 140 may execute a browser application to enable the user to request and view reports from the dossier change control management system 130 via the network 170. Various example reports are described in greater detail below, with reference to FIG. 2.

The data stores 120, dossier change control management system 130, and client devices 140 are configured to communicate via the network 170, which may include any combination of local area and/or wide area networks, using both wired and/or wireless communication systems. In one embodiment, the network 170 uses standard communications technologies and/or protocols. For example, the network 170 may include communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 170 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 170 may be represented using any suitable format, such as hypertext markup language (HTML) or extensible markup language (XML). In some embodiments, all or some of the communication links of the network 170 may be encrypted using any suitable technique or techniques.

Figure 2:
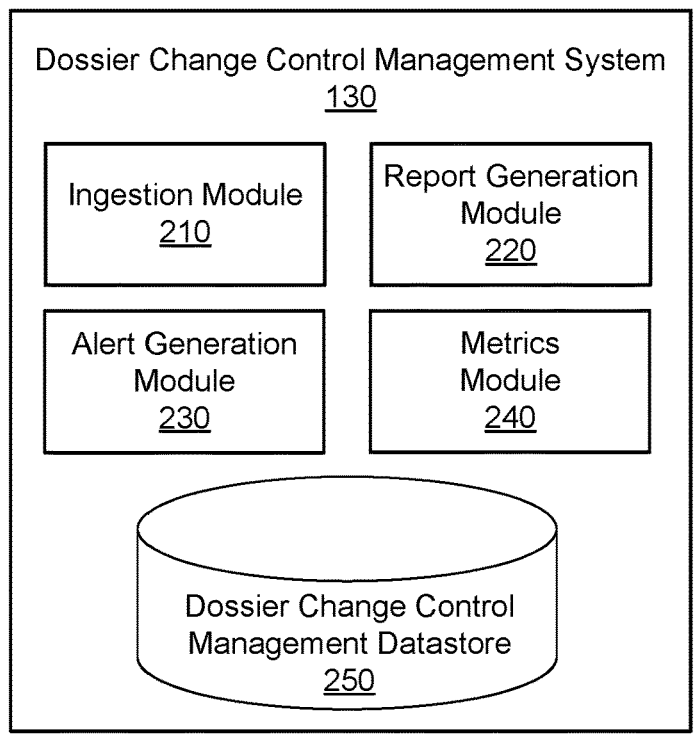
FIG. 2 is a block diagram of the dossier change control management system of FIG. 1, according to one embodiment.

FIG. 2 illustrates one embodiment of the dossier change control management system 130. In the embodiment shown, the dossier change control management system 130 includes an ingestion module 210, a report generation module 220, an alert generation module 230, a metrics module 240, and a dossier change control management datastore 250. In other embodiments, the dossier change control management system 130 contains different and/or additional elements. In addition, the functions may be distributed among the elements in a different manner than described.

The ingestion module 210 receives documents and corresponding metadata from the data stores 120. Note that, although the term "documents" is used for convenience, some the ingestion module 210 may also ingest raw data, such as metadata indicating the dates on which various tasks were completed, etc. The ingested documents may be automatically received from a data store 120 and/or manually identified by a user. In various embodiments, the ingestion module 210 periodically (e.g., every eight hours, daily, weekly, etc.) uses an extract transform load (ETL) process to retrieve new and updated documents from each connected data store 120 and add the documents to the dossier change control management data store 250. In one such embodiment, the ingestion process includes extracting information from the retrieved documents, identifying one or more dossiers (e.g., one or more pharmaceutical products) impacted by the extracted information, transforming the information into a standardized format, and adding the information regarding the identified dossiers to the dossier change control management datastore 250 (e.g., by updating the corresponding documents set 310, metadata 320, and/or product registration data 350).

The ingestion module 210 may also provide a user interface for providing documents for which automatic ingestion fails or is otherwise unavailable. For example, the user interface may be used to ingest historical documents that were not automatically ingested or to associate a document with an impacted dossier where the automated process failed to identify that the document is relevant to the dossier in question. Regardless of how the documents are provided, the ingestion module 210 analyzes the received documents to extract pertinent information. In one embodiment, the ingestion module 210 extracts information by identifying the type of the document and applying one or more mapping rules. A typical regulatory approval process involves the applicant and regulator exchanging sets of standard forms. The ingestion module 210 can identify the type of form (e.g., based on a form number, an arrangement of boxes, metadata associated with the form, or other expected features) and use mapping rules to extract the information from the form and transform it into a standardized format. The ingestion module 210 stores the extracted information (e.g., in the dossier change control management datastore 250). Additionally or alternatively, the information stored may include pointers and/or links to the underlying documents from which the information was extracted. Furthermore, in some embodiments, the ingestion module 210 may enable the user to delete or remove documents that were previously ingested.

Figure 3:
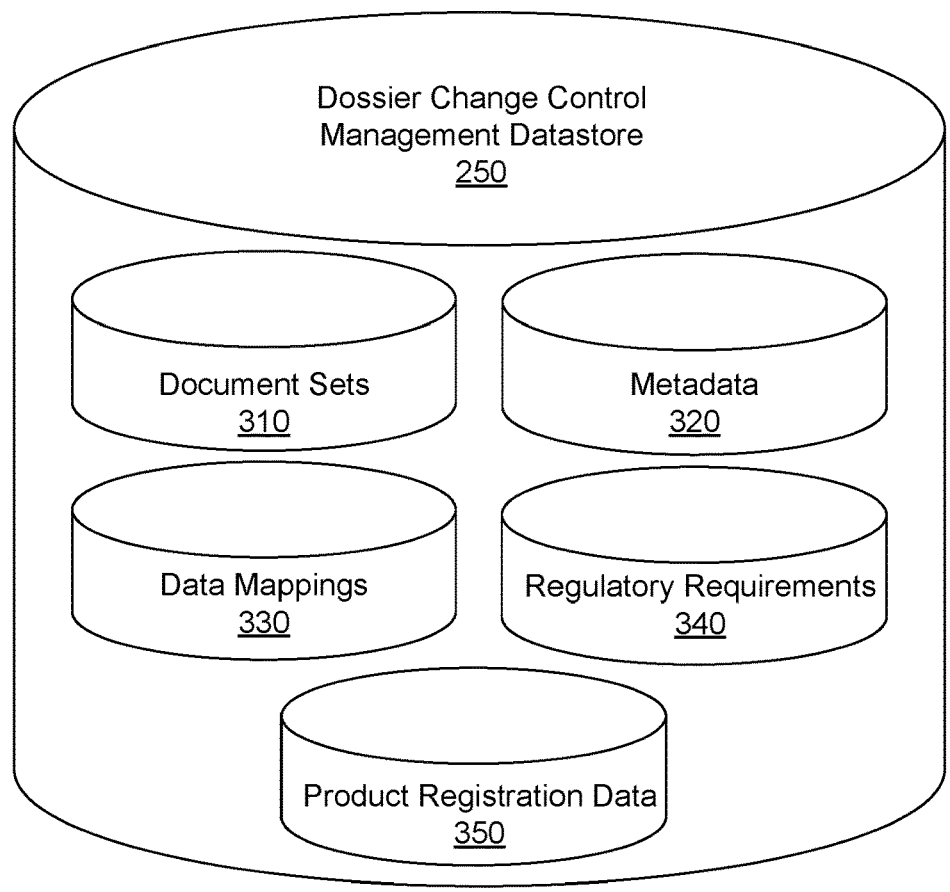
FIG. 3 is a block diagram of the dossier change control management database of FIG. 2, according to one embodiment.

The dossier change control management datastore 250 includes one or more computer readable media configured to store the data extracted and used by the dossier change control management system 130. Although it is shown as a single entity within the dossier change control management system 130, in some embodiments, the dossier change control management datastore is a distributed database that is accessed via the network 170. FIG. 3 illustrates one embodiment of the dossier change control management datastore 250 that stores document sets 310, metadata 320, data mappings 330, regulatory requirements 340, and product registration data 350. In other embodiments, the dossier change control management datastore 250 may store different or additional data. Furthermore, the data may be arranged differently. For example, although the document sets 310 and metadata 320 are shown as distinct sets of data for illustrative purposes, a document and the corresponding metadata may be stored as a single data object.

The document sets 310 include the information extracted by the ingestion module 210 indexed by pharmaceutical product. The information may also by indexed by jurisdiction, document type, date, and/or any other suitable field. For example, the dossier change control management system 130 may maintain a document set for each of the operating entity's pharmaceutical products in each jurisdiction that the pharmaceutical product is either approved for sale or going through a regulatory approval process. Each document set includes the relevant information for the corresponding product and jurisdiction. The document sets may also include revision histories for the documents. Thus, a user may check the status of a given document at a specified time in the past.

The metadata 320 contains information about the documents in the document sets 310 stored in association with the corresponding document or an identifier of the corresponding document. The metadata 320 may include: the identity of one or more people responsible for the document, the identity of one or more authors of the document, the entity that issued the document, one or more jurisdictions for which the document is relevant, a creation date for the document, a last edited date for the document, and the like.

The data mappings 330 map the information in ingested forms to a standardized format and define reports that the dossier change control management system 130 may generate. For ingested documents, the data mappings 330 indicate what information is included on different types of forms and where that information is located, enabling the dossier change control management system 130 to translate the document into a standardized format by mapping portions of the document to fields in a template for the standardized format. In the case of reports, the data mappings link particular fields of documents in the document sets 330 to fields in report templates. The generation of reports is described in greater detail below, with reference to the report generation module 220.

The regulatory requirements 340 indicate expected documents and steps for obtaining (and maintaining) regulatory approval of pharmaceutical products in each jurisdiction for which the dossier change control management system 130 is configured. The regulatory requirements 340 for a jurisdiction may include expected ingoing and outgoing forms or letters and expected content for each such forms and letters as well as rules for determining corresponding deadlines. For example, in one jurisdiction, an applicant may have six months after receiving a particular letter to provide a response. As another example, local regulations or practices in another jurisdiction may dictate that an applicant should expect as response from the regulator within three months of filing a particular form. The regulatory requirements 340 may also indicate expected information to be included in documents. For example, a standard form may include boxes or other regions for various pieces of information about the corresponding product, and the regulatory requirements 340 may indicate expected values (including potentially empty fields), types of data, formatting requirements, and the like.

The product registration data 350 provides histories of the progression of pharmaceutical products through the regulatory processes in each relevant jurisdiction. In one embodiment, the product registration data 350 indicates the history of documents in the document sets 310, including information such as submission dates, revisions made, the dates of and reasons for those revisions, and responsible individuals (e.g., who signed off on and/or submitted a document). For example, the product registration data 350 may include, for each document in a document set 310, the date on which it was approved for submission, the date it was actually submitted, the date the submission was approved by the regulatory agency, countries in which a pharmaceutical product has a registration history, one or more names for the pharmaceutical product, the dates and types of significant events in the regulatory process, the dates on which specified milestones were reached, one or more names or identifiers of events and/or submissions, revision dates and reasons, and the like.

Referring back to FIG. 2, the report generation module 220 generates reports based on the document sets 310 stored in the dossier change control management datastore 250. In various embodiments, the report generation module 220 supports multiple types of reports. A report of a given type is generated from a template that includes standard content (section headings, explanations, disclaimers, etc.) and one or more fields for data. The report generation module 220 uses the data mappings 330 to determine which data from the data stores 120 should be used to complete the data fields for a given report. Once a report has been generated, the report generation module 220 provides it to one or more client device 140 for display.

In one embodiment, the report generation module 220 provides a client device 140 with a user interface via which users can identify one or more pharmaceutical products, one or more jurisdictions, and a report type. The user may identify the pharmaceutical product using one or more of: a trade name, a generic name, a product identification number, or any other suitable identifier or identifying information. In some configurations, if the user provides one type of identification (e.g., the generic name) one or more other identifiers are automatically added to the user interface (e.g., by querying a set of identifier mappings that link different identifiers that correspond to the same pharmaceutical product). In a similar way, the report generation module 220 may aggregate documents that use different identifiers for the same pharmaceutical product and use the aggregated documents in generating the report.

The report generation module 220 generates the requested report and provides it to the requesting client device 140 for display. The report may include links or other controls to enable the user to access the underlying documents in the dossier change control management datastore 250 and/or one or more the datastores 220. Example report types include documents released by the controlling entities headquarters, health authority submitted documents, and documents extracted from one or more specified data stores 120.

The alert generation module 230 monitors ingested data and generates an alert on detection of an out-of-expectation scenario. An out-of-expectation scenario can be any fact or combination of facts that deviates from an expected regulatory process that suggests corrective action should be considered. For example, if a particular regulatory form must be filed by a certain date and company practice is to file it at least a threshold amount of time before of the deadline (e.g., one week), an alert may be generated if the form is not ingested from the appropriate data store 120 once the deadline in less than the threshold amount of time in the future. As another example, if a form is ingested but lacks one or more information items the corresponding mapping indicates should be present, or if the information included is invalid or incomplete, an alert may be generated identifying the missing or incomplete information.

In one embodiment, the alert generation module 230 periodically (e.g., weekly) generates a report identifying gaps in one or more document sets 310. These gaps may include any missing documents or information for which an alert has been generated that have not been addressed. The report may be provided to one or more client devices 140 for presentation in a user interface. When presented in the user interface, the report may include links to the underlying document sets 310 for which gaps are identified. The user interface may also provide controls for a user to address the gaps. For example, the user interface may include controls for adding a missing document to a document set 310, providing missing information, and/or correcting erroneous information. Any information provided by the user may be added to the dossier change control management datastore 250 and provided to the appropriate data store 120.

In another embodiment, in addition to or instead of generating periodic reports, the alert generation module 230 sends a notification of a gap to one or more responsible users (e.g., a regulatory compliance manager for the product) on identifying a gap. The notification may be displayed in a dedicated user interface provided for the dossier change control management system 130 at a client device 140. Additionally or alternatively, the notification may be sent via email, text message, or other suitable communication channel. The notification may include a link or other control to provide the user a report providing additional detail regarding the gap. Thus, a user receiving the alert may ensure the gap is addressed in a timely manner (e.g., before the deadline for filing a form passes). In some embodiments, the alert includes a suggestion of where missing data might be found (e.g., a suggested document for ingestion).

The metrics module 240 generates metrics indicating the quality or health of the datasets 310. In one embodiment, a user may select one or more pharmaceutical products (e.g., using a user interface of a client device 140) and the metrics module 240 generates a report including one or more metrics, such as the total number of documents in the correspond document set 310, the total number of documents submitted to regulators, the total number of documents received from regulators, the number of gaps identified, and the like. The metrics can be presented as raw numbers and/or in one or more charts. The metrics report may also include links to the underlying documents, either in the document set 310, datastores 120, or both.

In one embodiment, the metrics report is presented in a user interface of a client device 140. When presented in the user interface, the report may include controls to enable the user to drill down into the metrics. For example, the user may investigate what categories of documents or in which jurisdictions the majority of gaps are occurring to identify corrective measures that may be appropriate (e.g., a more rigorous business process for a certain jurisdiction or document type). The user interface may also include controls enabling the user to apply filters, resulting in the metrics being recalculated and the displayed report being updated. For example, a user may initially request a report for a product in all jurisdictions, and then apply a filter to look at the results for a single jurisdiction of interest. As another example, the user may filter based on date ranges to investigate a potential problem is a specific time period or analyze the evolution of the metrics for a product over time.

Example Methods

Figure 4:
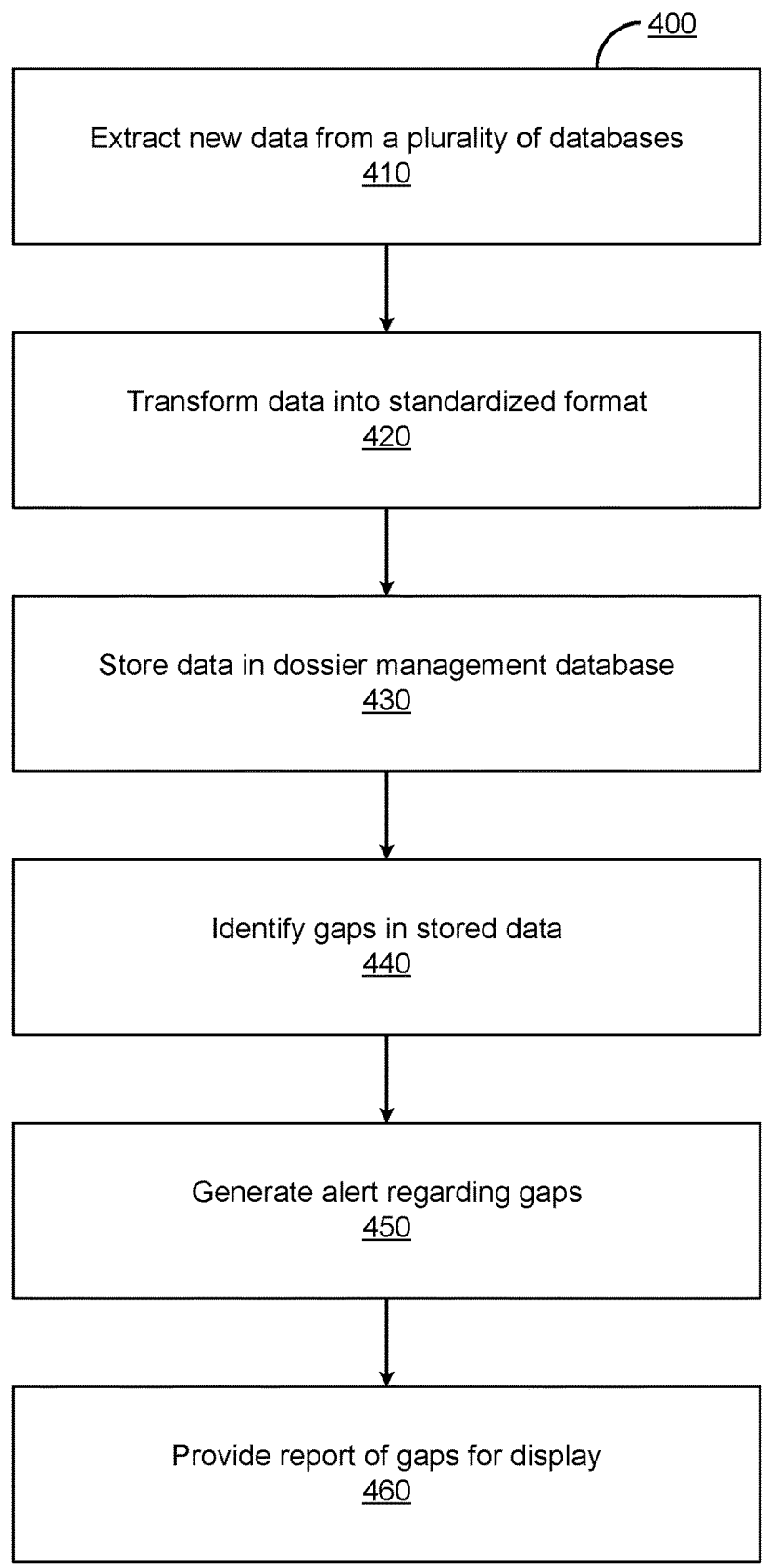
FIG. 4 is a flowchart of a process for importing dossier documents and identifying gaps, according to one embodiment.

FIG. 4 illustrates an example method 400 for importing documents and identifying gaps. The steps of FIG. 4 are illustrated from the perspective of various components of the dossier change control management system 130 performing the method 400. However, some or all of the steps may be performed by other entities and/or components. In addition, some embodiments may perform the steps in parallel, perform the steps in different orders, or perform different steps.

In the embodiment shown, the method 400 begins with the ingestion module 210 extracting 410 new data from two or more databases (e.g., datastores 120). As explained previously, the data may be extracted periodically using a scheduled data extraction process. The ingestion module 210 transforms 420 the data into a standardized format and stores 430 it in the dossier change control management database (e.g., within the dossier change control management datastore 250).

The alert generation module 230 identifies 440 gaps in the stored data. As described previously, a gap may be an expected document (e.g., as indicated by the regulatory requirements 340) that is missing or expected data fields within a document that are either missing, incomplete, or invalid. The alert generation module 230 generates one or more alerts regarding the identified gaps and provides 460 a corresponding report for display (e.g., at a client device 140). The user may then investigate and address the identified gaps (e.g., using a user interface in which the report is displayed).

Figure 5:
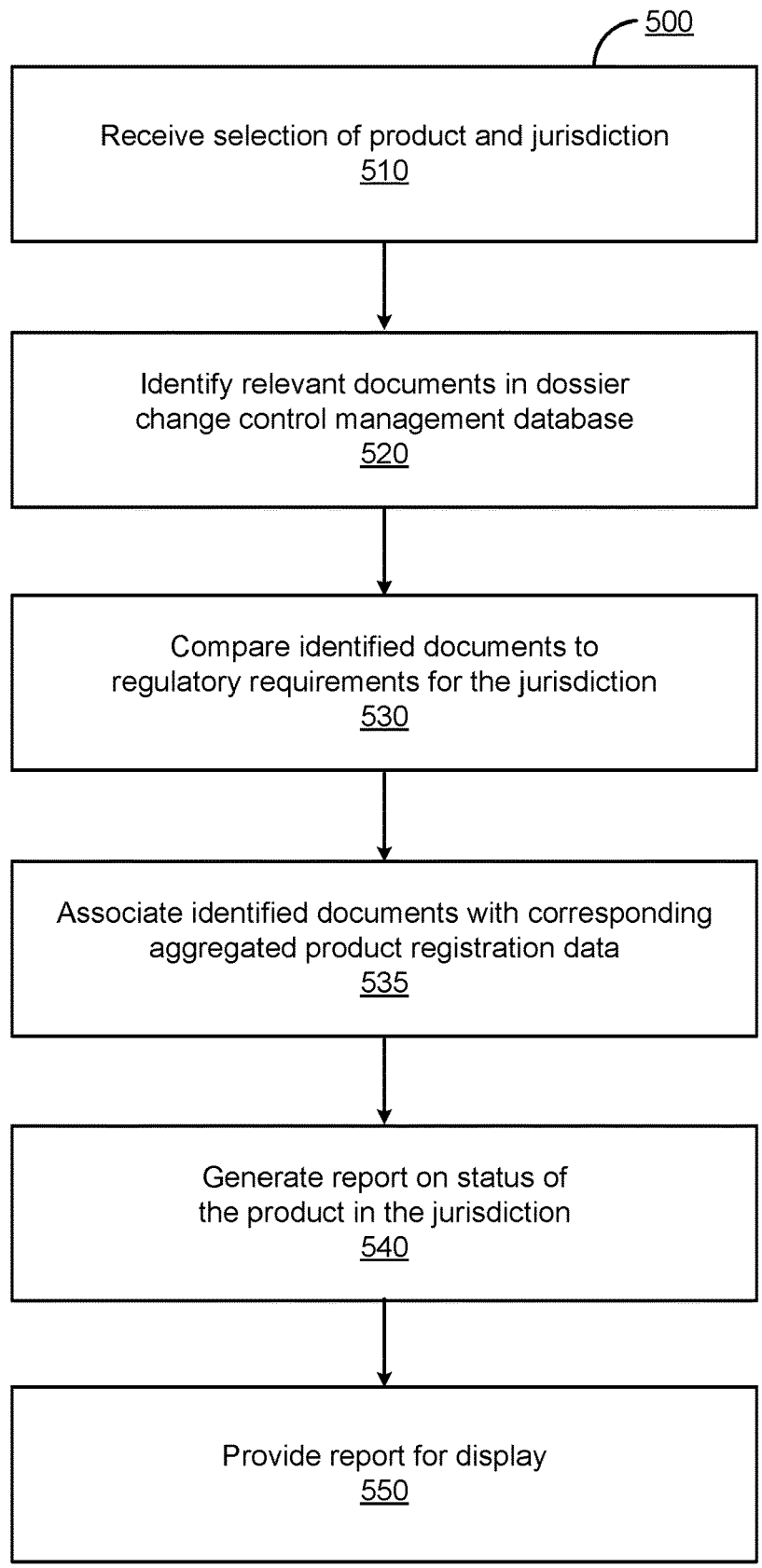
FIG. 5 is a flowchart of a process for generating a report, according to one embodiment.

FIG. 5 illustrates an example method 500 for generating a report regarding a pharmaceutical product in a jurisdiction. The steps of FIG. 5 are illustrated from the perspective of the report generation module 220 performing the method 500. However, some or all of the steps may be performed by other entities and/or components. In addition, some embodiments may perform the steps in parallel, perform the steps in different orders, or perform different steps.

In the embodiment shown in FIG. 5, the method 500 begins with the report generation module 220 receiving 510 a selection of a pharmaceutical product and jurisdiction. For example, a user may identify the product and jurisdiction via a user interface at a client device 140, which is provided to the report generation module 220 via the network 170. The report generation module 220 identifies 520 the relevant documents in the dossier change control management datastore 250 (i.e., those documents associated with the specified product in the given jurisdiction).

The report generation module 220 compares 530 the identified documents to the regulatory requirements 340 for the jurisdiction and associates 535 the identified documents with the corresponding product registration data 350 that is aggregated in the dossier change control management datastore 250. Thus, the report generation module 220 can identify what parts of the regulatory process have been complete, what actions remain outstanding, and the like. Based on this comparison, the report generation module 220 generates 540 a report on the status of the pharmaceutical product in the jurisdiction and provides 550 it for display at a client device 140. As described previously, different types of report may be generated 540, with each report being defined by a template and set of data mappings 330 between information in the document sets 310 and fields in the report template. In some embodiments, more advanced rules may be used, such as omitting or including sections of a report based on the current stage of the regulatory process the pharmaceutical product is in.

Figure 6:
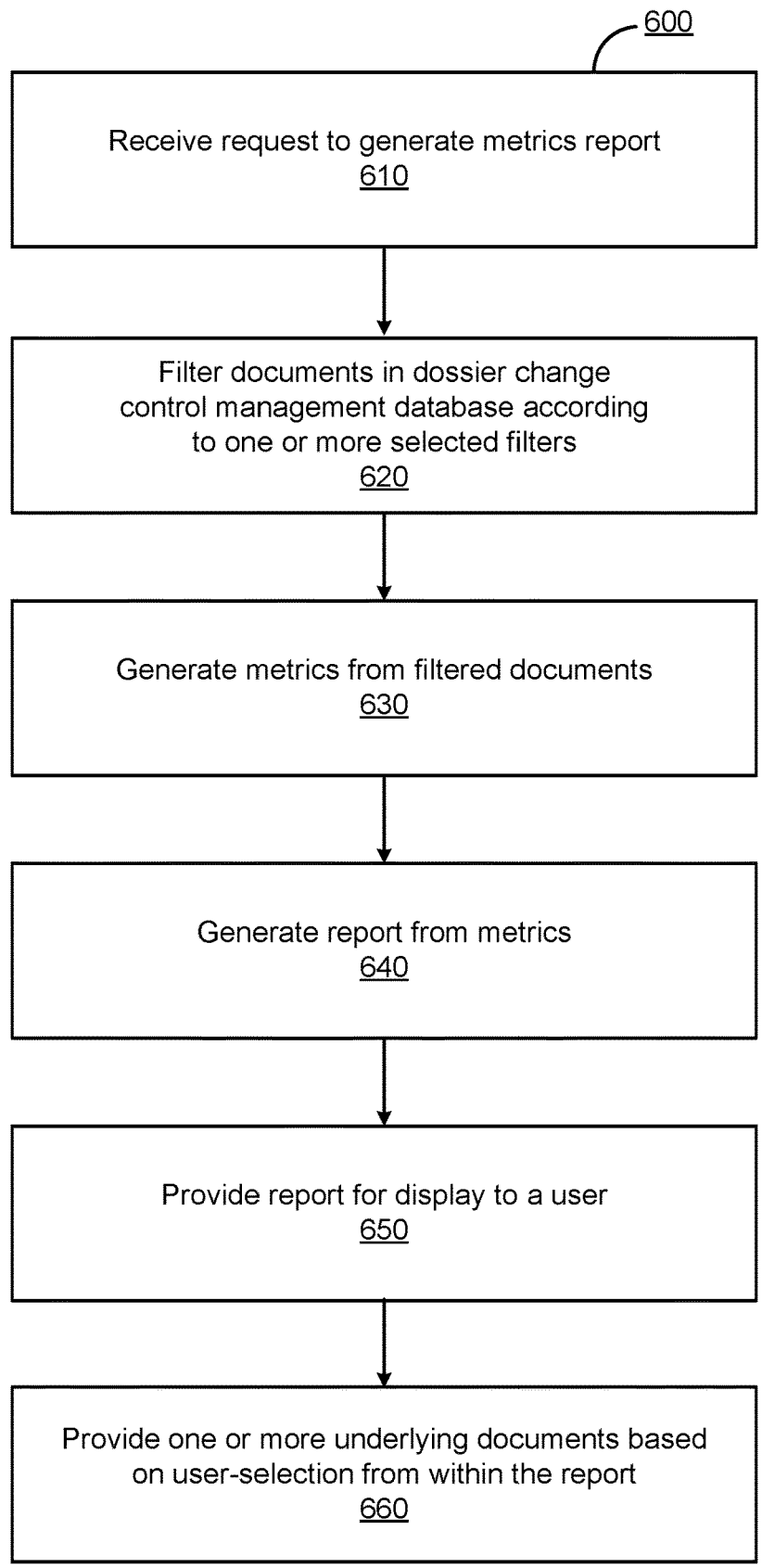
FIG. 6 is a flowchart of a process for providing a dossier metrics report including links to the underlying documents, according to one embodiment.

FIG. 6 illustrates an example method 600 for providing a dossier metrics report. The steps of FIG. 6 are illustrated from the perspective of the metrics module 240 performing the method 600. However, some or all of the steps may be performed by other entities and/or components. In addition, some embodiments may perform the steps in parallel, perform the steps in different orders, or perform different steps.

In the embodiment shown in FIG. 6, the method 600 begins with the metrics module 240 receiving 610 a request to generate a metrics report. In one embodiment, the request is generated by a client device 140 and in response to user input and sent to the metrics module 240 via the network 170. The user may also select one or more filters to apply, such as selecting a particular pharmaceutical product, identifying a jurisdiction, specifying a time range, and the like. The metrics module 240 filters 620 the documents in the dossier change control management datastore 250 according to the selected filters and generates 630 metrics from the filtered documents. As described previously, the metrics may include the total number of documents in the correspond document set 310, the total number of documents submitted to regulators, the total number of documents received from regulators, the number of gaps identified, and the like.

The metrics module 240 generates 640 a report from the metrics and provides 650 the report for display to the requesting user (e.g., by sending the report to the client device 40 from which the report request was received). The client device 140 my present the report to the user in a user interface. In one embodiment, the user interface also includes controls to drill down into the metrics (e.g., to apply further filters, separate the metrics out into different categories, and/or further breakdown the metrics in any other appropriate manner). The user interface may also enable the user to select specific documents (e.g., a document for which the metrics indicate a large number of gaps) and access 660 the selected document (from the dossier change control management datastore 250 and/or the original datastore 220 from which it was ingested). Thus, the user may be able to better evaluate the cause of gaps and take corrective action to reduce the number if future instances of gaps. One of skill in the art will recognize a wide range of ways in metrics may be generated and presented in reports to provide insight into the overall operation of the dossier change control management system 130.

Figure 7:
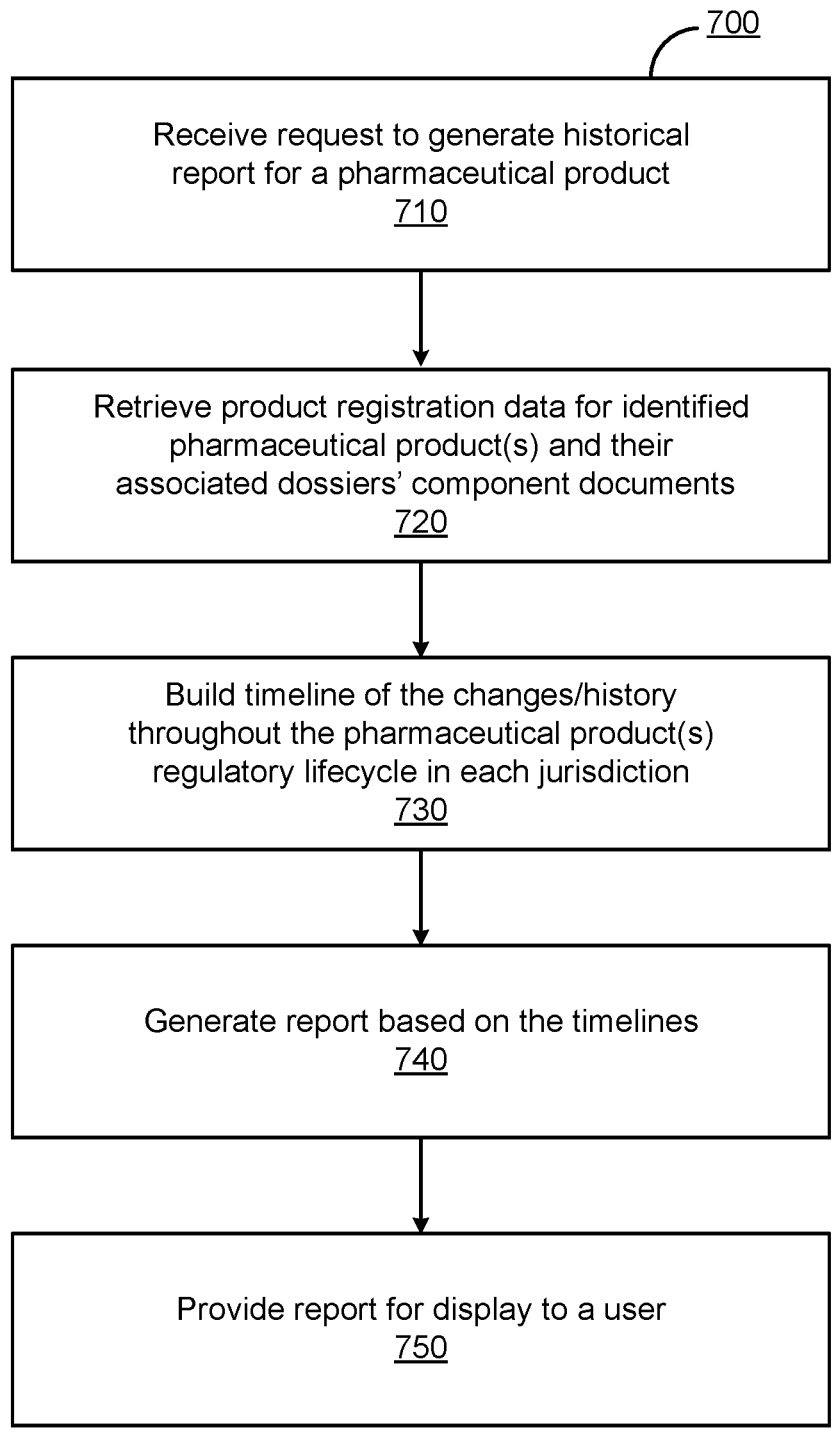
FIG. 7 is a flowchart of a process for providing a report on the regulatory history of a pharmaceutical product, according to one embodiment.

FIG. 7 illustrates an example method 700 for providing a report on the regulatory history of a pharmaceutical product. The steps of FIG. 7 are illustrated from the perspective of the report generation module 220 performing the method 700. However, some or all of the steps may be performed by other entities and/or components. In addition, some embodiments may perform the steps in parallel, perform the steps in different orders, or perform different steps.

In the embodiment shown in FIG. 7, the method 700 begins with the report generation module 220 receiving 710 a request to generate a historical report for a pharmaceutical product. The request identifies the pharmaceutical product using one or more identifiers (e.g., a generic or brand name provided by a user at a client device 140 when requesting the report). In some embodiments, the request may also one or more types of event of interest. Types of event may include dates on which the licensing process began in countries, dates of regulatory approval, clinical trial developments, unexpected results (e.g., reported stability issues), etc.

The report generation module 220 retrieves 720 the product registration data 350 for the identified pharmaceutical product. The report generation module 220 also retrieves 720 relevant document sets 310 and/or metadata 320 from the dossier(s). The retrieved data indicates which jurisdictions are relevant for the identified product (e.g., those in which regulatory approval has been obtained or is being sought for the pharmaceutical product). Based on the retrieved data, the report generation module 220 builds 730 a timeline of the changes/history of the dossier(s) throughout the pharmaceutical product's lifecycle in each relevant jurisdiction.

The report generation module 220 generates 740 a report based on the timelines and provides 750 the report for display to a user (e.g., at a client device 140). In one embodiment, the report includes all significant regulatory events for the pharmaceutical product in all relevant jurisdictions. Alternatively, the user may identify a particular event type of interest (either when making the original request or using user interface controls when viewing the report) and the report generation module 220 generates 740 a report indicating details of events of the specified type in each relevant jurisdiction. For example, by specifying initial regulatory submissions as the event type, the user may obtain a report that indicates the date on which an application to license the pharmaceutical product was first submitted in each relevant country. As another example, by specifying stability related submissions, the user may obtain a report identifying all regulatory submissions made throughout the world that relate to stability of the pharmaceutical product. Thus, if new data identifies a previously unknown stability problem, the user can quickly identify all jurisdictions and submissions for which updated filings should be considered. One of skill in the art will appreciate that a wide range of reports may be specified and generated in view of the context provided by the product registration data 350. As described previously, this data encapsulates what is in a dossier, when it was added, and why it was added, enabling a wide range of contextual reports to be generated.

Computing Machine Architecture

Figure 8:
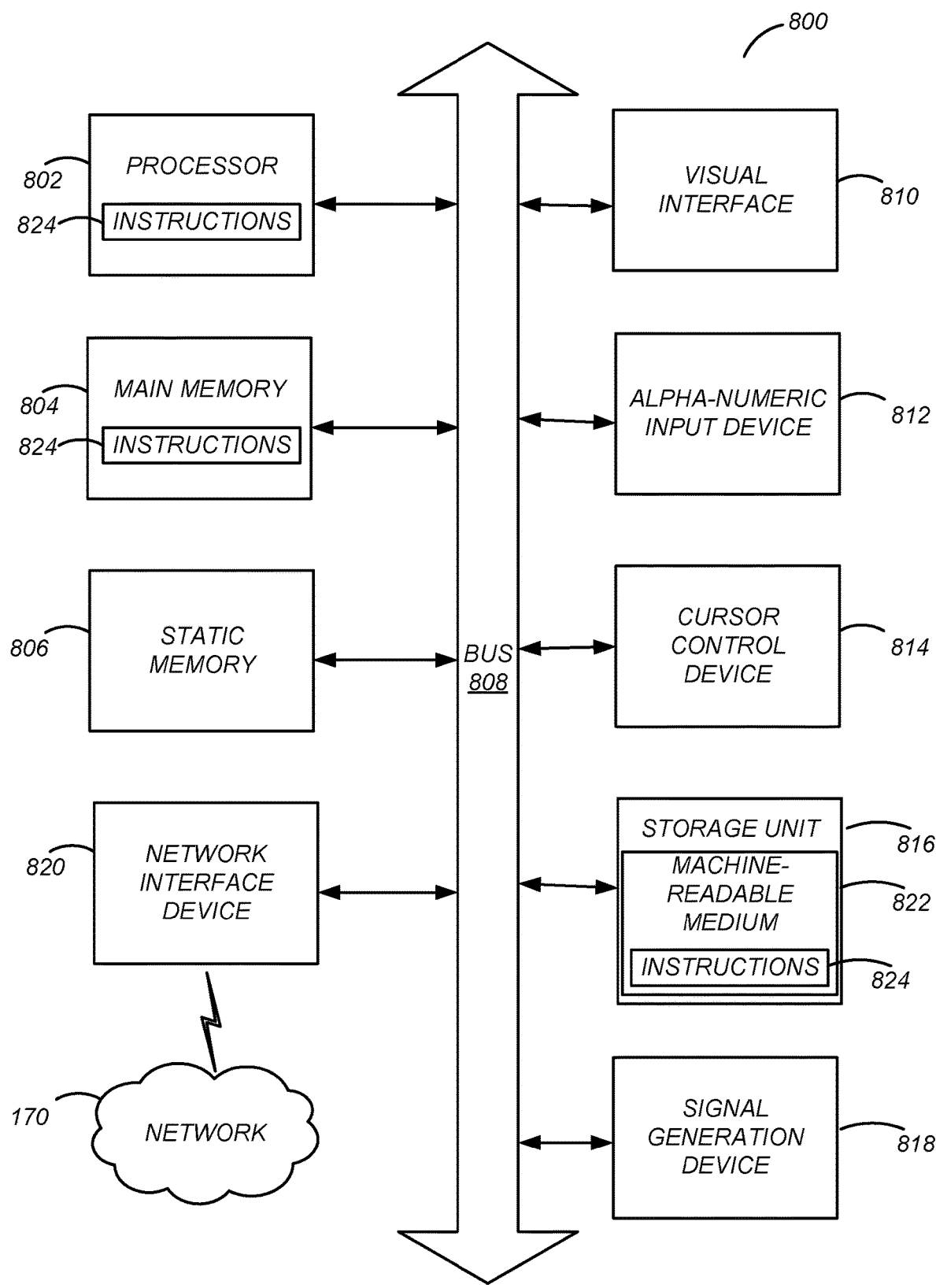
FIG. 8 a block diagram illustrating components of an example machine able to read instructions from a machine-readable medium and execute them in a processor (or controller), according to one embodiment.

FIG. 8 is a block diagram illustrating components of an example machine able to read instructions from a machine-readable medium and execute them in a processor (or controller). Specifically, FIG. 8 shows a diagrammatic representation of a machine in the example form a computer system 800, within which program code (e.g., software or software modules) for causing the machine to perform any one or more of the methodologies discussed herein may be executed. The program code may be comprised of instructions 824 executable by one or more processors 802. In alternative embodiments, the machine operates as a stand-alone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 824 (sequential or otherwise) that specify actions to be taken by that machine. Further, while only a single machine is illustrated, the term "machine" shall also be taken to include any collection of machines that individually or jointly execute instructions 824 to perform any one or more of the methodologies discussed herein.

The example computer system 800 includes a processor 802 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 804, and a static memory 806, which are configured to communicate with each other via a bus 808. The computer system 800 may further include visual display interface 810. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 810 may include or may interface with a touch enabled screen. The computer system 800 may also include alphanumeric input device 812 (e.g., a keyboard or touch screen keyboard), a cursor control device 814 (e.g., a mouse, a trackball, a joystick, a motion sensor, or other pointing instrument), a storage unit 816, a signal generation device 818 (e.g., a speaker), and a network interface device 820, which also are configured to communicate via the bus 808.

The storage unit 816 includes a machine-readable medium 822 on which is stored instructions 824 (e.g., software) embodying any one or more of the methodologies or functions described herein. The instructions 824 (e.g., software) may also reside, completely or at least partially, within the main memory 804 or within the processor 802 (e.g., within a processor's cache memory) during execution thereof by the computer system 800, the main memory 804 and the processor 802 also constituting machine-readable media. The instructions 824 (e.g., software) may be transmitted or received over a network 170 via the network interface device 820.

While machine-readable medium 822 is shown in an example embodiment to be a single medium, the term "machine-readable medium" should be taken to include a single medium or multiple media (e.g., a centralized or distributed database, or associated caches and servers) able to store instructions (e.g., instructions 824). The term "machine-readable medium" shall also be taken to include any medium that is capable of storing instructions (e.g., instructions 824) for execution by the machine and that cause the machine to perform any one or more of the methodologies disclosed herein. The term "machine-readable medium" includes, but not be limited to, data repositories in the form of solid-state memories, optical media, and magnetic media.

ADDITIONAL CONFIGURATION CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across one or more machines, e.g. computer system 800. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. It should be noted that where an operation is described as performed by "a processor," this should be construed to also include the process being performed by more than one processor. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for a dossier change control management system through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented dossier change control management method for a set of regulated products, the method comprising:
periodically ingesting data regarding at least a plurality of the regulated products from a plurality of data stores, the ingested data including documents;
transforming, based on a data mapping, a subset of the documents into a standardized format, wherein transforming each document in the subset of documents into the standardized format includes:
analyzing the document to identify a type of the document;
selecting, based on the type of the document, the data mapping from a plurality of possible data mappings, each of the possible data mappings corresponding to a different type of document; and
mapping, using the data mapping, portions of the document to fields of a template for the standardized format;
for each regulated product of the plurality of regulated products,
aggregating, in a dossier change control management database, dossier data associated with the regulated product including the subset of documents associated with the regulated product in the standardized format, the dossier data for the regulated product describing a regulatory history of the regulated product;
responsive to newly ingested data indicating a change that impacts a regulatory requirement of the regulated product, updating, in the dossier change control management database, the dossier data describing the regulatory history of the regulated product using the received data;
identifying, based on the dossier data and regulatory requirement data indicating information expected to be included in the dossier, an out-of-expectation scenario for the dossier;
generating an alert responsive to identifying the out-of-expectation scenario; and
providing, for display at a client device, a report based on the alert, the report including information about the out-of-expectation scenario derived from the dossier change control management database.

2. The computer-implemented dossier change control management method of claim 1, wherein identifying the out-of-expectation scenario comprises:
identifying, from the regulatory requirement data, an expected document that should be present in the dossier; and
determining that the expected document is not present in the dossier, wherein the out-of-expectation scenario is the expected document being missing from the dossier.

3. The computer-implemented dossier change control management method of claim 2, wherein identifying the expected document that should be present in the dossier comprises:
determining a regulatory deadline for filing the expected document with a regulator;
comparing the regulatory deadline to a current date; and
determining the expected document should be present responsive to the current date being less than a threshold amount of time before the regulatory deadline.

4. The computer-implemented dossier change control management method of claim 1, wherein identifying the out-of-expectation scenario comprises:
identifying an expected document that is present in the dossier;
identifying expected metadata to be included in the dossier data in view of the expected document; and
determining, by analyzing the dossier data, that the expected metadata is missing, incomplete, or invalid, wherein the out-of-expectation scenario is the expected metadata being missing, incomplete, or invalid.

5. The computer-implemented dossier change control management method of claim 1, wherein the report is generated periodically and identifies out-of-expectation scenarios identified since a previous instance of the report was generated.

6. The computer-implemented dossier change control management method of claim 1, wherein the report includes one or more links that provide access to at least some of the ingested data in the plurality of data stores.

7. The computer-implemented dossier change control management method of claim 1, further comprising sending, to the client device, a notification of the alert, wherein the report is provided to the client device responsive to user interaction with the notification.

8. The computer-implemented dossier change control management method of claim 1, further comprising:
receiving a request to generate a second report, the request identifying the regulated product and a jurisdiction;
identifying relevant data for the jurisdiction in the dossier of the regulated product;
comparing the relevant data to data indicating regulatory requirements for the jurisdiction;
generating, based on the comparison, a report regarding a current regulatory status of the regulated product in the jurisdiction; and
providing the report to the client device for display.

9. The computer-implemented dossier change control management method of claim 1, further comprising:
receiving, from the client device, a request for a metrics report;
generating the metrics report; and
providing, for display at the client device, the metrics report, wherein the metrics report includes one or more links that provide access to at least some of the ingested data in the plurality of data stores.

10. The computer-implemented dossier change control management method of claim 1, wherein the regulated product is a pharmaceutical product.

11. The method of claim 1, wherein the ingested data includes structured and unstructured data.

12. A non-transitory computer-readable medium storing computer program code, the computer program code comprising instructions that, when executed by a computer system, cause the computer system to:
periodically ingest data regarding at least a plurality of regulated products from a plurality of data stores, the ingested data including documents;
transform, based on a data mapping, a subset of the documents into a standardized format, wherein the instructions that cause the computer system to transform each document in the subset of documents into the standardized format include instructions that cause the computer system to:
analyze the document to identify a type of the document;
select, based on the type of the document, the data mapping from a plurality of possible data mappings, each of the possible data mappings corresponding to a different type of document; and map, using the data mapping, portions of the document to fields of a template for the standardized format;

for each regulated product of the plurality of regulated products, aggregate, in a dossier change control management database, dossier data associated with the regulated product including the subset of documents associated with the regulated product in the standardized format, the dossier data for the regulated product describing a regulatory history of the regulated product;

responsive to newly ingested data indicating a change that impacts a regulatory requirement of the regulated product, update, in the dossier change control management database, the dossier data describing the regulatory history for of the regulated product using the received data;

identify, based on the dossier data and regulatory requirement data indicating information expected to be included in the dossier, an out-of-expectation scenario for the dossier;

generate an alert based on the out-of-expectation scenario; and provide, for display at a client device, a report based on the alert, the report including information about the out-of-expectation scenario derived from the dossier change control management database.

13. The non-transitory computer-readable medium of claim 12, wherein the instructions that cause the computer system to identify the out-of-expectation scenario comprise instructions that cause the computer system to:

identify, from the regulatory requirement data, an expected document;

determine a regulatory deadline for filing the expected document with a regulator;

compare the regulatory deadline to a current date;

determine the expected document should be present responsive to the current date being less than a threshold amount of time before the regulatory deadline; and determine that the expected document is not present in the dossier, wherein the out-of-expectation scenario is the expected document being missing from the dossier.

14. The non-transitory computer-readable medium of claim 12, wherein the instructions that cause the computer system to identify the out-of-expectation scenario comprise instructions that cause the computer system to:

identify an expected document that is present in the dossier;

identify expected metadata to be in the dossier data in view of the expected document; and determine, by analyzing the dossier data, that the expected metadata is missing, incomplete, or invalid, wherein the out-of-expectation scenario is the expected metadata being missing, incomplete, or invalid.

15. The non-transitory computer-readable medium of claim 12, wherein the report includes one or more links that provide access to at least some of the ingested data in the plurality of data stores.

16. The non-transitory computer-readable medium of claim 12, wherein the instructions further comprise instructions that cause the computer system to:

send, to the client device, a notification of the alert;

receive, from the client device, an indication that the user interacted with the notification; and provide, to the client device, the report responsive to the indication.

17. The non-transitory computer-readable medium of claim 12, wherein the instructions further cause the computer system to:

receive a request to generate a second report, the request identifying the regulated product and a jurisdiction;

identify relevant data for the jurisdiction in the dossier of the regulated product;

compare the relevant data to data indicating regulatory requirements for the jurisdiction;

generate, based on the comparison, a report regarding a current regulatory status of the regulated product in the jurisdiction; and provide the report to the client device for display.

18. The non-transitory computer-readable medium of claim 12, wherein the instructions further cause the computer system to:

receive, from the client device, a request for a metrics report;

generate the metrics report; and provide, for display at the client device, the metrics report, wherein the metrics report includes one or more links that provide access to at least some of the ingested data in the plurality of data stores.

19. The non-transitory computer-readable medium of claim 12, wherein the ingested data includes structured and unstructured data.

* * * * *